United States Patent
Graves et al.

(10) Patent No.: US 9,801,968 B2
(45) Date of Patent: Oct. 31, 2017

(54) LIGHTED AIR FRESHENER ASSEMBLY

(71) Applicants: Cherie Graves, Gustine, CA (US);
Katy Graves, Gustine, CA (US);
Andrew Graves, Gustine, CA (US)

(72) Inventors: Cherie Graves, Gustine, CA (US);
Katy Graves, Gustine, CA (US);
Andrew Graves, Gustine, CA (US)

( * ) Notice: Subject to any disclaimer, the term of this patent is extended or adjusted under 35 U.S.C. 154(b) by 195 days.

(21) Appl. No.: 14/658,420

(22) Filed: Mar. 16, 2015

(65) Prior Publication Data

US 2016/0271286 A1     Sep. 22, 2016

(51) Int. Cl.
| A61L 9/12 | (2006.01) |
| F21S 9/02 | (2006.01) |
| F21S 10/02 | (2006.01) |
| F21V 33/00 | (2006.01) |

(52) U.S. Cl.
CPC .............. *A61L 9/12* (2013.01); *A61L 9/127* (2013.01); *A61L 2209/12* (2013.01); *F21S 9/02* (2013.01); *F21S 10/02* (2013.01); *F21V 33/0004* (2013.01)

(58) Field of Classification Search
CPC .......... F21S 9/02; F21S 10/02; F21V 33/0004
USPC .................... 362/95, 96, 234, 253
See application file for complete search history.

(56) References Cited

U.S. PATENT DOCUMENTS

| 5,556,192 | A | 9/1996 | Wang |
| D508,557 | S | 8/2005 | Morrill |
| 7,232,251 | B2 | 6/2007 | Chien |
| 7,277,626 | B2 | 10/2007 | Pesu et al. |
| 7,687,037 | B2 | 3/2010 | Wheatley et al. |
| 7,821,765 | B2 | 10/2010 | Kinsey |
| 7,934,845 | B2 * | 5/2011 | Yang ................ F21S 6/001 362/101 |
| 8,133,440 | B2 * | 3/2012 | Jorgensen ............. A61L 9/14 239/34 |
| 2008/0130266 | A1 * | 6/2008 | DeWitt .................. A61L 9/03 362/96 |
| 2009/0122516 | A1 * | 5/2009 | Yang .................. A61L 9/122 362/96 |
| 2010/0270943 | A1 * | 10/2010 | Cook .................... A61L 9/03 315/291 |
| 2012/0020052 | A1 * | 1/2012 | McCavit ............ A61L 9/122 362/96 |
| 2012/0318780 | A1 | 12/2012 | Juarez |
| 2013/0170184 | A1 * | 7/2013 | Browder ............ A61L 9/015 362/96 |
| 2013/0223043 | A1 * | 8/2013 | Ray .................... F21V 33/00 362/96 |
| 2015/0070874 | A1 * | 3/2015 | Beesley ......... H05B 33/0803 362/96 |

* cited by examiner

*Primary Examiner* — Laura Tso

(57) ABSTRACT

A lighted air freshener assembly provides a fragranced odor and illumination as well as the ability to be hung from a support structure, such as a Christmas tree. The assembly includes a support base having a top wall, a bottom wall and a perimeter wall coupled to and extending between the top wall and the bottom wall. At least one light emitter is coupled to the support base. A scent device is coupled to the support base and includes a scented material for emitting a fragranced odor. A decorative casing is positionable over the scent device and is removably couplable to the support base.

15 Claims, 4 Drawing Sheets

LIGHTED AIR FRESHENER ASSEMBLY

BACKGROUND OF THE DISCLOSURE

Field of the Disclosure

The disclosure relates to air freshener devices and more particularly pertains to a new air freshener device for providing a fragranced odor and illumination as well as the ability to be hung from a support structure, such as a Christmas tree.

SUMMARY OF THE DISCLOSURE

An embodiment of the disclosure meets the needs presented above by generally comprising a support base having a top wall, a bottom wall and a perimeter wall coupled to and extending between the top wall and the bottom wall. At least one light emitter is coupled to the support base. A scent device is coupled to the support base and includes a scented material for emitting a fragranced odor. A decorative casing is positionable over the scent device and is removably couplable to the support base.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
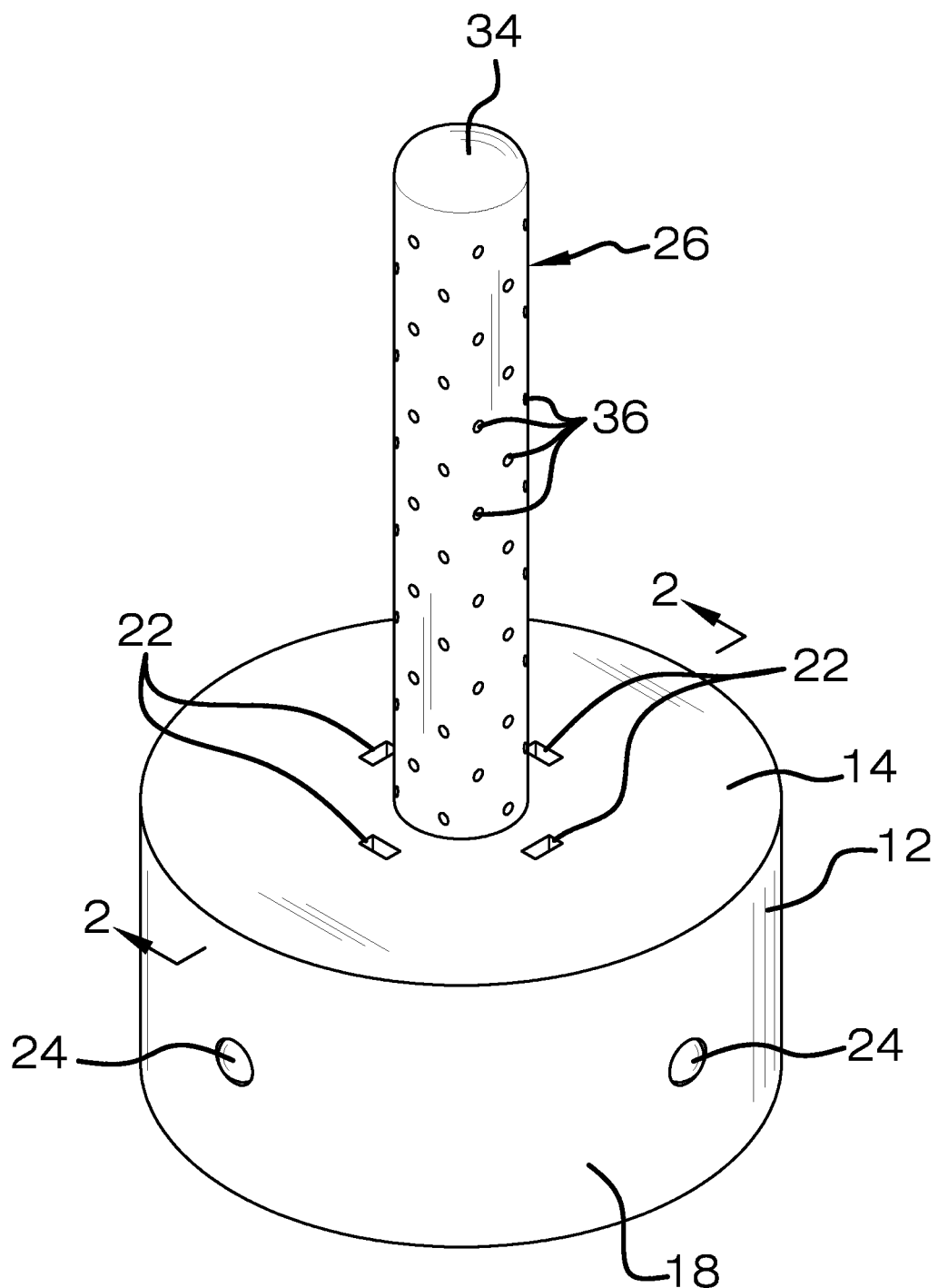
FIG. 1 is a top front side perspective view of a support base and a scent device of a lighted air freshener assembly according to an embodiment of the disclosure.
Figure 2:
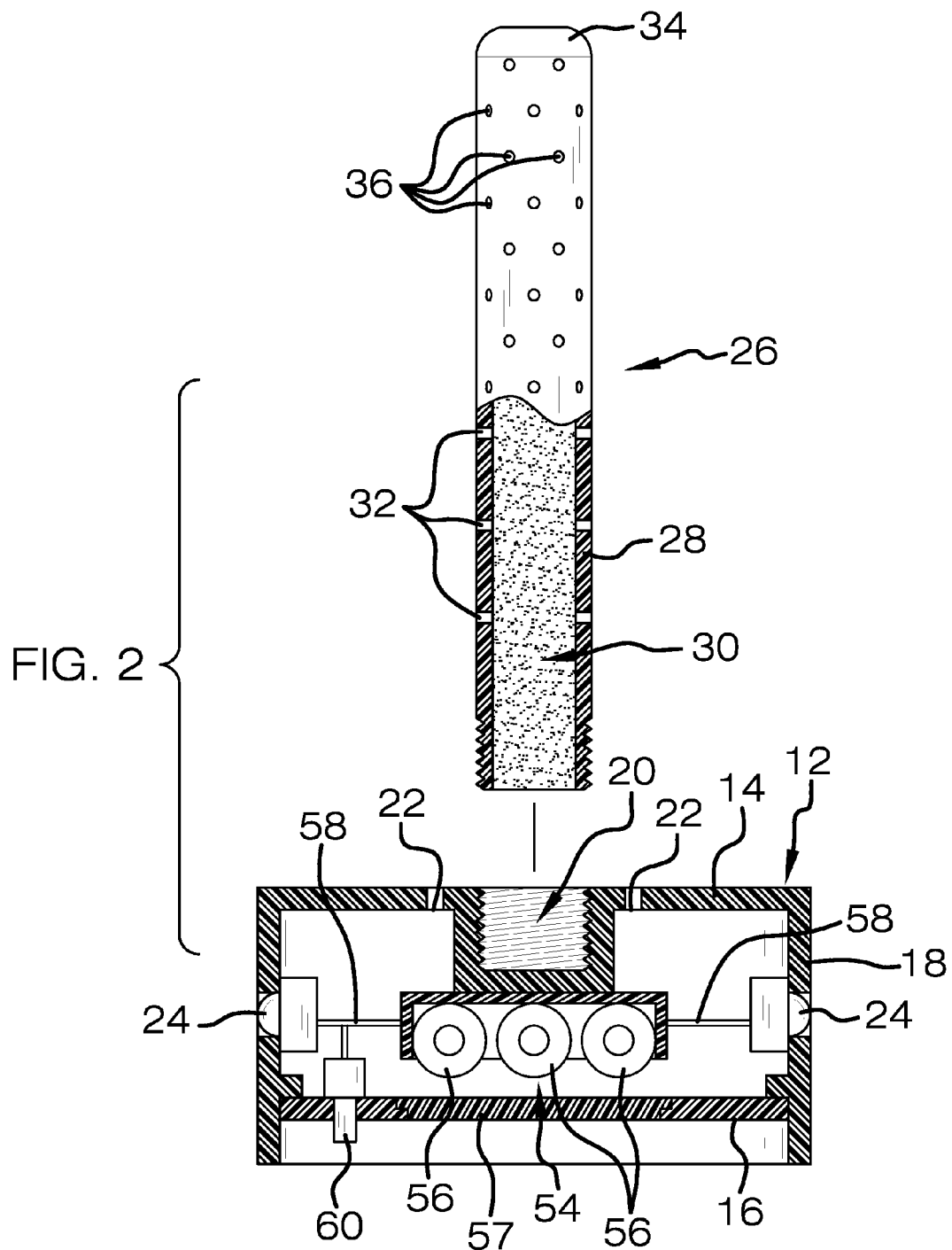
FIG. 2 is a cross-sectional view of an embodiment of the disclosure taken along line 2-2 of FIG. 1.
Figure 3:
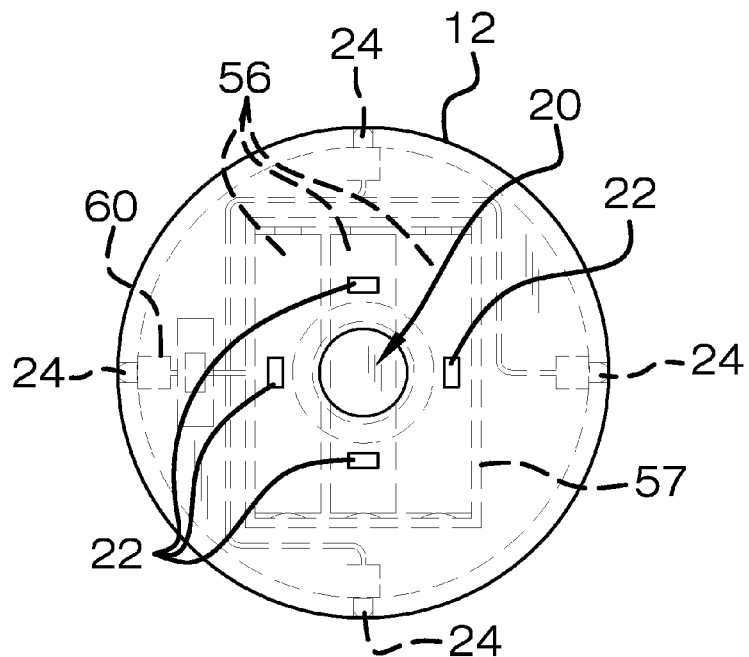
FIG. 3 is a top view of the support base of an embodiment of the disclosure.
Figure 4:
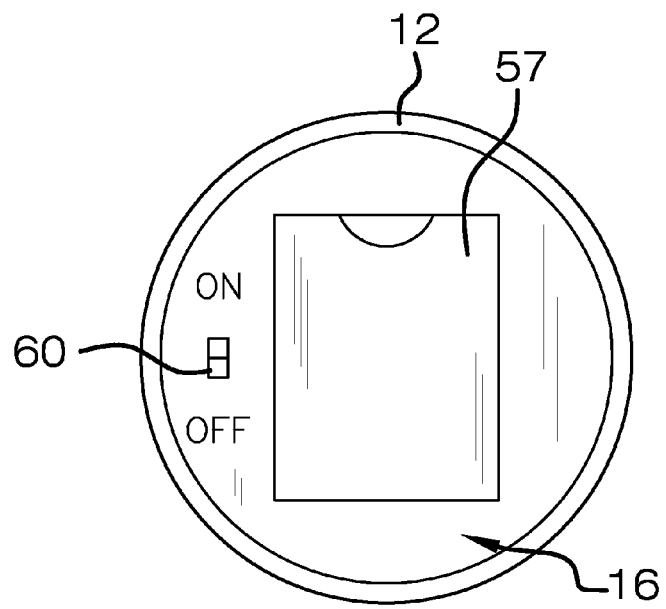
FIG. 4 is a bottom view of the support base of an embodiment of the disclosure.
Figure 5:
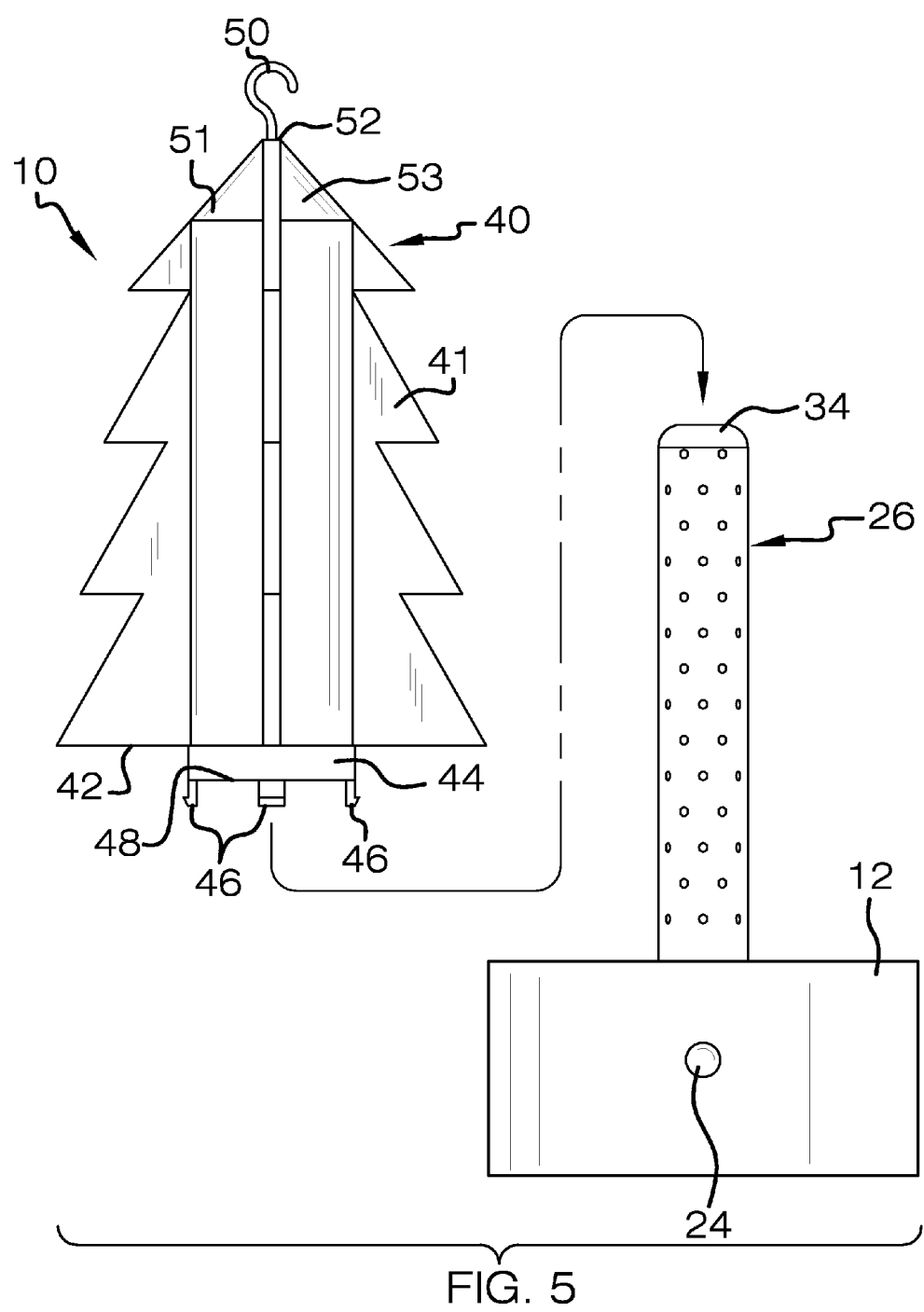
FIG. 5 is a front view of an embodiment of the disclosure.

With reference now to the drawings, and in particular to FIGS. 1 through 5 thereof, a new air freshener device embodying the principles and concepts of an embodiment of the disclosure and generally designated by the reference numeral 10 will be described.

As best illustrated in FIGS. 1 through 5 the lighted air freshener assembly 10 generally comprises a support base 12 having a top wall 14, a bottom wall 16 and a perimeter wall 18 coupled to and extending between the top wall 14 and the bottom wall 16. The top wall 14 of the support base 12 has a cavity 20 and a plurality of slots 22 extending therein.

A plurality of light emitters 24 is coupled to the support base 12. More particularly, each light emitter 24 is coupled to the perimeter wall 18 and may be spaced uniformly around the perimeter wall 18. Each light emitter 24 may comprise a color-changing light-emitting diode.

A scent device 26 is coupled to the support base 12. The scent device 26 is positionable in the cavity 20 for supporting the scent device 26 on the support base 12. The scent device 26 is threadably couplable to the cavity 20. The scent device 26 includes an elongated tube 28 and a scented material 30. The scented material 30 is positioned within an interior of the tube 28 for emitting a fragranced odor. The tube 28 has a plurality of openings 32 positioned therein along a length of the tube 28 for permitting the fragranced odor emitted by the scented material 30 to escape through the openings 32. A sleeve 34 is positioned over the tube 28 wherein the sleeve 34 covers the tube 28. The sleeve 34 has a plurality of holes 36 positioned therein for dispersing the fragranced odor emitted by the scented material 30.

A decorative casing 40 is positionable over the scent device 26. The decorative casing 40 is removably couplable to the support base 12. The decorative casing 40 includes a main body 41 having a bottom end 42. The main body 41 may have a themed shape, such as resembling the shape of a Christmas tree, a shamrock or the like. A flange 44 is coupled to and extends downwardly from the bottom end 42. A plurality of tabs 46 is coupled to and extends downwardly from a bottom 48 of the flange 44. Each of the tabs 46 is insertable into an associated one of the slots 22 for removably coupling the decorative casing 40 to the support base 12. A hook 50 is coupled to a top end 52 of the main body 41 of the decorative casing 40 to facilitate hanging of the assembly 10. The decorative casing 40 further includes a pair of spaced panels 51, 53 coupled to the main body 41 and positioned parallel with respect to each other. The panels 51, 53 extend from the top end 52 to the bottom end 42 of the main body 41.

A power source 54 is coupled to the support base 12. The power source 54 is electrically coupled to each light emitter 24 for providing electrical current to each light emitter 24. The power source 54 may comprise at least one battery 56 and/or a power cord for electrically coupling to an electrical outlet. In the event that the power source 54 comprises one or more batteries 56, a cover 57 may be positionable over the batteries 56. Wiring 58 electrically couples the power source 54 to each light emitter 24. An actuator 60 electrically couples the power source 54 to each light emitter 24 for turning on each light emitter 24.

In use, the scent device 26 is coupled to the support base 12 in the cavity 20 of the support base 12. The actuator 60 is manipulated to turn on the light emitters 24. The scent device 26 emits a fragranced odor to freshen an external environment. The assembly 10 can placed upon a supporting surface, such as a desk, table or the like. Alternatively, the decorative casing 40 can be positioned over the scent device 26 and can be attached to the support base 12 by inserting the tabs 46 into the slots 22. This allows the assembly 10 be hung from hook 50.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. A lighted air freshener assembly comprising:
   a support base having a top wall, a bottom wall and a perimeter wall coupled to and extending between said top wall and said bottom wall;
   at least one light emitter coupled to said support base;
   a scent device coupled to said support base, said scent device including a scented material for emitting a fragranced odor; and
   a decorative casing positionable over said scent device, said decorative casing being removably couplable to said support base, said decorative casing including a main body having a top end, a hook being coupled to said top end of said main body to facilitate hanging of said assembly.

2. A lighted air freshener assembly comprising:
   a support base having a top wall, a bottom wall and a perimeter wall coupled to and extending between said top wall and said bottom wall;
   at least one light emitter coupled to said support base;
   a scent device coupled to said support base, said scent device including a scented material for emitting a fragranced odor;
   a decorative casing positionable over said scent device, said decorative casing being removably couplable to said support base;
   said top wall of said support base having a plurality of slots positioned therein;
   said decorative casing including a main body having a bottom end, a flange being coupled to and extending downwardly from said bottom end of said main body; and
   a plurality of tabs coupled to and extending downwardly from a bottom of said flange, each of said tabs being insertable into an associated one of said slots for removably coupling said decorative casing to said support base.

3. The assembly of claim 1, further comprising said light emitter being one of a plurality of said light emitters.

4. The assembly of claim 1, further comprising said light emitter being coupled to said perimeter wall.

5. The assembly of claim 3, further comprising each said light emitter being coupled to said perimeter wall, said light emitters being spaced uniformly around said perimeter wall.

6. The assembly of claim 1, further comprising said light emitter being a color-changing light emitter.

7. The assembly of claim 1, further comprising a power source coupled to said support base, said power source being electrically coupled to each said light emitter for providing electrical current to each said light emitter.

8. The assembly of claim 7, further comprising wherein said power source comprises at least one battery.

9. The assembly of claim 7, further comprising wiring electrically coupling said power source to each said light emitter.

10. The assembly of claim 7, further comprising an actuator electrically coupling said power source to each said light emitter for turning on each said light emitter.

11. A lighted air freshener assembly comprising:
    a support base having a top wall, a bottom wall and a perimeter wall coupled to and extending between said top wall and said bottom wall;
    at least one light emitter coupled to said support base;
    a scent device coupled to said support base, said scent device including a scented material for emitting a fragranced odor;
    a decorative casing positionable over said scent device, said decorative casing being removably couplable to said support base; and
    wherein said scent device includes
        an elongated tube, said scented material being positioned within an interior of said tube, said tube having a plurality of openings positioned therein along a length of said tube for permitting the fragranced odor emitted by said scented material to escape through said openings; and
        a sleeve positioned over said tube wherein said sleeve covers said tube, said sleeve having a plurality of holes positioned therein for dispersing the fragranced odor emitted by said scented material.

12. The assembly of claim 1, further comprising said top wall of said support base having a cavity extending therein, said scent device being positionable in said cavity for supporting said scent device on said support base.

13. The assembly of claim 11, further comprising said top wall of said support base having a cavity extending therein, said scent device being positionable in said cavity for supporting said scent device on said support base, said scent device being threadably couplable to said cavity.

14. A lighted air freshener assembly comprising:
    a support base having a top wall, a bottom wall and a perimeter wall coupled to and extending between said top wall and said bottom wall;
    at least one light emitter coupled to said support base;
    a scent device coupled to said support base, said scent device including a scented material for emitting a fragranced odor;
    a decorative casing positionable over said scent device, said decorative casing being removably couplable to said support base; and
    said decorative casing including a main body and a pair of spaced panels coupled together, said panels being positioned parallel with respect to each other, said panels extending from a top end to a bottom end of said main body.

15. The assembly of claim 1, further comprising:
    said top wall of said support base having a plurality of slots positioned therein, said top wall of said support base having a cavity extending therein;
    said at least one light emitter being included in a plurality of light emitters coupled to said support base, each said light emitter being coupled to said perimeter wall, said light emitters being spaced uniformly around said perimeter wall, each said light emitter being a color-changing light emitter;
    said scent device being positionable in said cavity for supporting said scent device on said support base, said scent device being threadably couplable to said cavity, said scent device including;

an elongated tube;

said scented material being positioned within an interior of said tube, said tube having a plurality of openings positioned therein along a length of said tube for permitting the fragranced odor emitted by said scented material to escape through said openings; and a sleeve positioned over said tube wherein said sleeve covers said tube, said sleeve having a plurality of holes positioned therein for dispersing the fragranced odor emitted by said scented material;

said decorative casing including a pair of spaced panels coupled together, said panels being positioned parallel with respect to each other, said panels extending from said top end to a bottom end of said main body, a flange being coupled to and extending downwardly from said bottom end of said main body;

a plurality of tabs coupled to and extending downwardly from a bottom of said flange, each of said tabs being insertable into an associated one of said slots for removably coupling said decorative casing to said support base;

a power source coupled to said support base, said power source being electrically coupled to each said light emitter for providing electrical current to each said light emitter, said power source comprising at least one battery;

wiring electrically coupling said power source to each said light emitter; and an actuator electrically coupling said power source to each said light emitter for turning on each said light emitter.

\* \* \* \* \*